US006696272B1

(12) United States Patent
Mahuran et al.

(10) Patent No.: US 6,696,272 B1
(45) Date of Patent: Feb. 24, 2004

(54) PRODUCTS AND METHODS FOR GAUCHER DISEASE THERAPY

(75) Inventors: Don J. Mahuran, Toronto (CA); Joe T. R. Clarke, Toronto (CA); John W. Callahan, Mississauga (CA)

(73) Assignee: HSC Research & Development Limited Partnership (CA)

( * ) Notice: Subject to any disclaimer, the term of this patent is extended or adjusted under 35 U.S.C. 154(b) by 37 days.

(21) Appl. No.: 09/586,216

(22) Filed: Jun. 2, 2000

Related U.S. Application Data

(60) Provisional application No. 60/137,598, filed on Jun. 3, 1999.

(30) Foreign Application Priority Data

Jun. 2, 1999 (CA) ............................................. 2272055

(51) Int. Cl.[7] .......................... C12P 21/06; C07H 21/04; C12N 15/00; C12N 15/63; A01N 63/00

(52) U.S. Cl. .................... 435/69.1; 435/320.1; 435/325; 435/455; 424/93.21; 536/23.2; 536/23.5

(58) Field of Search ............................. 536/23.2, 23.5; 435/325, 320.1, 455, 69.1; 424/93.21

(56) References Cited

U.S. PATENT DOCUMENTS

| | | | |
|---|---|---|---|
| 5,234,811 A | 8/1993 | Beutler et al. ................. 435/6 |
| 5,240,846 A | 8/1993 | Collins et al. ........... 435/240.1 |
| 5,266,459 A | 11/1993 | Beutler .......................... 435/6 |
| 5,399,346 A | 3/1995 | Anderson et al. ........ 424/93.21 |
| 5,436,146 A | 7/1995 | Shenk et al. ............. 435/172.3 |
| 5,529,774 A | 6/1996 | Barba et al. ............. 424/93.21 |
| 5,547,932 A | 8/1996 | Curiel et al. ................... 435/65 |
| 5,549,892 A | 8/1996 | Friedman et al. ........ 424/94.61 |
| 5,645,829 A | 7/1997 | Shockley et al. ........ 424/93.21 |
| 5,656,465 A | 8/1997 | Panicali et al. .......... 435/172.3 |
| 5,670,488 A | 9/1997 | Gregory et al. ................ 514/44 |
| 5,672,344 A | 9/1997 | Kelley et al. ............. 424/93.21 |
| 5,741,486 A | 4/1998 | Pathak et al. ............. 424/93.21 |
| 5,911,983 A | 6/1999 | Barranger et al. ....... 424/93.21 |

OTHER PUBLICATIONS

Rudinger; Characteristics of the amino acids as components of a peptide hormone sequence 1976, PEPTIDE HORMONES:1–7.*
Kaye et. al.; A single amino acid substitution results in a retinoblastoma protein defective in phosphorylation and oncoprotein binding, 1990, Proc. Natl. Acad. Sci., vol. 87:6922–6926.*
Skolnick et al., 2000, TIBTECH, vol. 18, p. 34–39.*
Rosenthal et al., Enzyme Replacement Therapy for Gaucher Disease: Skeletal Responses to Macrophage–targeted Glucocerebrosidase, *Pediatrics* (1995), 96:629–37.
Beutler et al., Enzyme–replacement Therapy for Gaucher's Disease, *N. Engl. J. Med.* (1991), 325:1809–10.
Tybulewicz et al., Animal Model of Gaucher's Disease from Targeted Disruption of the Mouse Glucocerebrosidase Gene, *Nature* (1992), 357:407–10.
Nolta et al., Retroviral–mediated Transfer of the Human Glucocerebrosidase Gene into Cultured Gaucher Bone Marrow, *J. Clin. Invest.* (1992), 90:342–48.
Needleman, S. B. and C. D. Wunsch, A General Method Applicable to the Search for Similarities in the Amino Acid Sequence of Two Proteins, *J. Mol. Biol.* (1970), 48:443–53.
Liu et al., Long–term Expression, Systemic Delivery, and Macrophage Uptake of Recombinant Human Glucocerebrosidase in Mice Transplanted with Genetically Modified Primary Myoblasts, *Hum. Gene Ther.* (1998), 9:2375–84.
Tsai et al., Allogenic Bone Marrow Transplantation in Severe Gaucher Disease, *Pediatr. Res.* (1992), 31:503–07.
Barton et al., Dose–dependent Responses to Macrophase–targeted Glucocerebrosidase in a Child with Gaucher Disease, *J. Pediatr.* (1992), 120:277–80.
Dunbar et al., Retroviral Transfer of the Glucocerebrosidase Gene into CD34+ Cells from Patients with Gaucher Disease: In Vivo Detection of Transduced Cells without Myeloablation, *Hum. Gene Ther.* (1998), 9:2629–40.
Havenga et al., Development of Safe and Efficient Retroviral Vectors for Gaucher Disease, *Gene Ther.* (1997), 4:1393–1400.
Havenga et al., In Vivo Methotrexate Selection of Murine Hemopoietic Cells Transduced with a Retroviral Vector for Gaucher Disease, *Gene Ther.* (1999), 6:1661–69.
Sidransky et al., *N. Engl. J. Med.* (1993), 328:1566.
Liu et al., Long–term Expression and Secretion of Human Glucocerebrosidase by Primary Murine and Human Myoblasts and Differentiated Myotubes, *J. Mol. Med.* (1998), 76:773–81.
Pasmanik–Chor et al., Expression of Mutated Glucocerebrosidase Alleles in Human Cells, *Hum. Mol. Genetics* (1997), 6:887–95.
Xu, Y. and G. A. Grabowski, Translational Inefficiency of Acid β–Glucosidase mRNA in Transgenic Mammal Cells, *Molecular Genetics and Metabolism* (1998), 64:87–98.
Xu, Y. and G. A. Grabowski, Molecular Cloning and Characterization of a Translational Inhibitory Protein that Binds to Coding Sequences of Human Acid β–Glucosidase and Other mRNAs, *Molecular Genetics and Metabolism* (1999), 68:441–54.

(List continued on next page.)

*Primary Examiner*—Shin-Lin Chen
(74) *Attorney, Agent, or Firm*—Synnestvedt & Lechner LLP

(57) ABSTRACT

The invention relates to products and methods for medical treatment of Gaucher disease and, in particular, an improved Gcc DNA for insertion into any applicable expression vector for gene therapy treatment. The invention includes an isolated Gcc DNA molecule, wherein nucleic acid molecules have been modified at cryptic splice sites to prevent or decrease splicing of mRNA produced from the DNA molecule, while preserving the ability of the DNA to express functional Gcc polypeptides.

17 Claims, 11 Drawing Sheets

OTHER PUBLICATIONS

Brady et al., Modifying Exogenous Glucocerebrosidase for Effective Replacement Therapy in Gaucher Disease, *J. Inher. Metab. Dis* (1994), 17:510–19.

Fallet et al., Enzyme Augmentation in Moderate to Life-threatening Gaucher Disease, *Pediatr. Res.* (1992), 31:496–502.

Grabowski et al., Enzyme Therapy in Type 1 Gaucher Disease: Comparative Efficacy of Mannose–terminated Glucocerebrosidase from Natural and Recombinant Sources, *Ann. Intern. Med.* (1995), 122:33–39.

Kozak, M., At Least Six Nucleotides Preceding the AUG Initiator Codon Enhance Translation in Mammalian Cells, *J. Mol. Biol.* (1987), 947–50.

Krawczak et al., The Mutational Spectrum of Single Base–pair Substitution in mRNA Splice Junctions of Human Genes: Causes and Consequences, *Hum. Genet.* (1992), 90:41–54.

Chomczynski, P. and N. Sacchi, Single–step Method of RNA Isolation by Acid Guanidium Thiocyanate–Phenol–Chloroform Extraction, *Analytical Biochemistry* (1987), 162:156–59.

Maquat, L. E., Defects in RNA Splicing and the Consequence of Shortened Translational Reading Frames, *Am. J. Hum. Genet.* (1996), 59:279–86.

Schuening, F., Retrovirus–mediated Transfer of the cDNA for Human Glucocerebrosidase into Peripheral Blood Repopulating Cells of Patients with Gaucher's Disease, *Hum. Gene Ther.* (1997), 8:2143–60.

\* cited by examiner

Full Length:

Properly Spliced:

Downstream Missplice:

Unsplice Intron and Downstream Missplice:

▬ Upstream Splice Site (part of the expression vector)

▬ 'Weird' Splice Site (found in the Gcc cDNA sequence)

r rAG/ qua aqu    Consensus Donor

5'- AAG CCG TTG AGT AGG/ GTA AGC ATC ATG GCT GGC AGC CTC AC   160- a) unmodified Gcc

| Lys Pro Leu Ser Arg Val Ser Ile Met Ala Gly Ser Leu Thr   26 |

5'- AAG CCG TTG AGT AGA GTC TCC ATC ATG GCT GGC AGC CTC AC   160-
              *    *  ** b) "modifi4ed Gcc"

yyy yyy yyy ync aq/G    Consensus Acceptor

5'- TTT CCT GCC CTT GGT ACC TTC AG/C CGC TAT GAG AGT ACA C   340- a) unmodified Gcc

| Phe Pro Ala Leu Gly Thr Phe Ser Arg Tyr Glu Ser Thr Arg |
| 83 |

5' TTT CCT GCC CTG GGA ACA TTT TCC CGC TAT GAG AGT ACA C   340-
            *   *   *  *  **

Fig. 3A b) modified Gcc

Product of Alternatively Spliced mRNA transcript from the unmodified Gcc cDNA:

NOTE:

Nucleotides associated with RNA splice-sites are underlined. Those believed to be of most importance to splice site-recognition are double underlined.

"/" in Consensus Splice Sequence indicates splice site. "*" under a particular nucleotide indicates a base changed in the site-directed mutagenesis procedure.

r = C or A, y = c or u, and n = any.

Fig. 3B

Partial produce of the crypic splicing of Gcc cDNA

5'- AAG CCG TTG AGT AGG CCG CTA TGA GAG TAC AC

Lys Pro Leu Ser Arg[16] Pro Leu STOP[20]!!

NotI
```
NGCGGCCGCTTAGCT TGACTTAAGAAGGCC GACGCCATGGAGTTT TCAAGTCCTTCCAGA   60
                                    MetGluPhe     SerSerProSerArg

GAGGAATGTCCCAAG CCGTTGAGTAGGGTA AGCATCATGGCTGGC AGCCTCACAGGTTTG  120
GluGluCysProLys ProLeuSerArgVal SerIleMetAlaGly SerLeuThrGlyLeu

CTTCTACTTCAGGCA GTGTCGTGGGCATCA GGTGCCCGCCCCTGC ATCCCTAAAAGCTTC  180
LeuLeuLeuGlnAla ValSerTrpAlaSer GlyAlaArgProCys IleProLysSerPhe

GGCTACAGCTCGGTG GTGTGTGTCTGCAAT GCCACATACTGTGAC TCCTTTGACCCCCCG  240
GlyTyrSerSerVal ValCysValCysAsn AlaThrTyrCysAsp SerPheAspProPro

AOCTTTCCTGCCCTT GGTAGCTTCAGCCGC TATGAGAGTACACGC AGTGGGCGACGGATG  300
ThrPheProAlaLeu GlyThrPheSerArg TyrGluSerThrArg SerGlyArgArgMet

GAGCTGAGTATGGGG CCCATCCAGGCTAAT CACACGGGCACAGGC CTGCTACTGACCCTG  360
GluLeuSerMetGly ProIleGlnAlaAsn HisThrGlyThrGly LeuLeuLeuThrLeu

CAGCCAGAACAGAAG TTCCAGAAAGTGAAG GGATTTGGAGGGGCC ATGACAGATGCTGCT  420
GlnProGluGlnLys PheGlnLysValLys GlyPheGlyGlyAla MetThrAspAlaAla

GCTCTCAACATCCTT GCCCTGTCACCCCCT GCCCAAAATTTGCTA CTTAAATCGTACTTC  480
AlaLeuAsnIleLeu AlaLeuSerProPro AlaGlnAsnLeuLeu LeuLysSerTyrPhe

TCTGAAGAAGGAATC GGATATAACATCATC CGGGTACCCATGGCC AGCTGTGACTTCTCC  540
SerGluGluGlyIle GlyTyrAsnIleIle ArgValProMetAla SerCysAspPheSer

ATCCGCACCTACACC TATGCAGACACCCCT GATGATTTCCAGTTG CACAACTTCAGCCTC  600
IleArgThrTyrThr TyrAlaAspThrPro AspAspPheGlnLeu HisAsnPheSerLeu

CCAGAGGAAGATACC AAGCTCAAGATACCC CTGATTCACCGAGCC CTGCAGTTGGCCCAG  660
ProGluGluAspThr LysLeuLysIlePro LeuIleHisArgAla LeuGlnLeuAlaGln

CGTCCCGTTTCACTC CTTGCCAGCCCCTGG ACATCACCCACTTGG CTCAAGACCAATGGA  720
ArgProValSerLeu LeuAlaSerProTrp ThrSerProThrTrp LeuLysThrAsnGly
```

| | | | | |
|---|---|---|---|---|
| GCGGTGAATGGGAAG | GGGTCACTCAAGGGA | CAGCCCGGAGACATC | TACCACCAGACCTGG | 780 |
| AlaValAsnGlyLys | GlySerLeuLysGly | GlnProGlyAspIle | TyrHisGlnThrTrp | |
| GCCAGATACTTTGTG | AAGTTCCTGGATGCC | TATGCTGAGCACAAG | TTACAGTTCTGGGCA | 840 |
| AlaArgTyrPheVal | LysPheLeuAspAla | TyrAlaGluHisLys | LeuGlnPheTrpAla | |
| GTGACAGCTGAAAAT | GAGCCTTCTGCTGGG | CTGTTGAGTGGATAC | CCCTTCCAGTGCCTG | 900 |
| ValThrAlaGluAsn | GluProSerAlaGly | LeuLeuSerGlyTyr | ProPheGlnCysLeu | |
| GGCTTCACCCCTGAA | CATCAGCGAGACTTA | ATTGCCCGTGACCTA | GGTCCTACCCTCGCC | 960 |
| GlyPheThrProGlu | HisGlnArgAspLeu | IleAlaArgAspLeu | GlyProThrLeuAla | |
| AACAGTACTCACCAC | AATGTCCGCCTACTC | ATGCTGGATGACCAA | CGCTTGCTGCTGCCC | 1020 |
| AsnSerThrHisHis | AsnValArgLeuLeu | MetLeuAspAspGln | ArgLeuLeuLeuPro | |
| CACTGGGCAAAGGTG | GTACTGACAGACCCA | GAAGCAGCTAAATAT | GTTCATGGCATTGCT | 1080 |
| HisTrpAlaLysVal | ValLeuThrAspPro | GluAlaAlaLysTyr | ValHisGlyIleAla | |
| GTACATTGGTACCTG | GACTTTCTGGCTCCA | GCCAAAGCCACCCTA | GGGGAGACACACCGC | 1140 |
| ValHisTrpTyrLeu | AspPheLeuAlaPro | AlaLysAlaThrLeu | GlyGluThrHisArg | |
| CTGTTCCCCAACACC | ATGCTCTTTGCCTCA | GAGGCCTGTGTGGGC | TCCAAGTTCTGGGAG | 1200 |
| LeuPheProAsnThr | MetLeuPheAlaSer | GluAlaCysValGly | SerLysPheTrpGlu | |
| CAGAGTGTGCGGCTA | GGCTCCTGGGATCGA | GGGATGCAGTACAGC | CACAGCATCATCACG | 1260 |
| GlnSerValArgLeu | GlySerTrpAspArg | GlyMetGlnTyrSer | HisSerIleIleThr | |
| AACCTCCTGTACCAT | GTGGTCGGCTGGACC | GACTGGAACCTTGCC | CTGAACCCCGAAGGA | 1320 |
| AsnLeuLeuTyrHis | ValValGlyTrpThr | AspTrpAsnLeuAla | LeuAsnProGluGly | |
| GGACCCAATTGGGTG | CGTAACTTTGTCGAC | AGTCCATCATTGTA | GACATCACCAAGGAC | 1380 |
| GlyProAsnTrpVal | ArgAsnPheValAsp | SerProIleIleVal | AspIleThrLysAsp | |
| ACGTTTTACAAACAG | CCCATGTTCTACCAC | CTTGGCCATTTCAGC | AAGTTCATTCCTGAG | 1440 |
| ThrPheTyrLysGln | ProMetPheTyrHis | LeuGlyHisPheSer | LysPheIleProGlu | |

```
GGCTCCCAGAGAGTG  GGGCTGGTTGCCAGT  CAGAAGAACGACCTG  GACGCAGTGGCATTG   1500
GlySerGlnArgVal  GlyLeuValAlaSer  GlnLysAsnAspLeu  AspAlaValAlaLeu

ATGCATCCCGATGGC  TCTGCTGTTGTGGTC  GTGCTAAACCGCTCC  TCTAAGGATGTGCCT   1560
MetHisProAspGly  SerAlaValValVal  ValLeuAsnArgSer  SerLysAspValPro

CTTACCATCAAGGAT  CCTGCTGTGGGCTTC  CTGGAGACAATCTCA  CCTGGCTACTCCATT   1620
LeuThrIleLysAsp  ProAlaValGlyPhe  LeuGluThrIleSer  ProGlyTyrSerIle

CACACCTACCTGTGG  CATCGCCAGTGATGG  AGCAGATACTCAAGG  AGGCACTGGGCTCAG   1680
HisThrTyrLeuTrp  HisArgGln

NotI
CCTGGGCATTAAAGG  GACAGAGTCAGCGAA  TTCTGCAGATATCCA  TCACACTGGCGGCCG   1740

```
            10          20          30          40          50          60
    123456789012345 678901234567890 123456789012345 678901234567890
         NotI
         ▽
    NGCGGCCGCTTAGCT TGACTTAAGAAGGCC GACGCCATGGAGTTT TCAAGTCCTTCCAGA      60
                                       MetGluPhe   SerSerProSerArg

GAGGAATGTCCCAAG CCGTTGAGTAGAGTC TCCATCATGGCTGGC AGCCTCACAGGTTTG     120
    GluGluCysProLys ProLeuSerArgVal SerIleMetAlaGly SerLeuThrGlyLeu

CTTCTACTTCAGGCA GTGTCGTGGGCATCA GGTGCCCGCCCCTGC ATCCCTAAAAGCTTC     180
    LeuLeuLeuGlnAla ValSerTrpAlaSer GlyAlaArgProCys IleProLysSerPhe

GGCTACAGCTCGGTG GTGTGTGTCTGCAAT GCCACATACTGTGAC TCCTTTGACCCCCCG     240
    GlyTyrSerSerVal ValCysValCysAsn AlaThrTyrCysAsp SerPheAspProPro

ACCTTTCCTGCCCTG GGAACATTTTCCCGC TATGAGAGTACACGC AGTGGGCGACGGATG     300
    ThrPheProAlaLeu GlyThrPheSerArg TyrGluSerThrArg SerGlyArgArgMet

GAGCTGAGTATGGGG CCCATCCAGGCTAAT CACACGGGCACAGGC CTGCTACTGACCCTG     360
    GluLeuSerMetGly ProIleGlnAlaAsn HisThrGlyThrGly LeuLeuLeuThrLeu

CAGCCAGAACAGAAG TTCCAGAAAGTGAAG GGATTTGGAGGGGCC ATGACAGATGCTGCT     420
    GlnProGluGlnLys PheGlnLysValLys GlyPheGlyGlyAla MetThrAspAlaAla

GCTCTCAACATCCTT GCCCTGTCACCCCCT GCCCAAAATTTGCTA CTTAAATCGTACTTC     480
    AlaLeuAsnIleLeu AlaLeuSerProPro AlaGlnAsnLeuLeu LeuLysSerTyrPhe

TCTGAAGAAGGAATC GGATATAACATCATC CGGGTACCCATGGCC AGCTGTGACTTCTCC     540
    SerGluGluGlyIle GlyTyrAsnIleIle ArgValProMetAla SerCysAspPheSer

ATCCGCACCTACACC TATGCAGACACCCCT GATGATTTCCAGTTG CACAACTTCAGCCTC     600
    IleArgThrTyrThr TyrAlaAspThrPro AspAspPheGlnLeu HisAsnPheSerLeu

CCAGAGGAAGATACC AAGCTCAAGATACCC CTGATTCACCGAGCC CTGCAGTTGGCCCAG     660
    ProGluGluAspThr LysLeuLysIlePro LeuIleHisArgAla LeuGlnLeuAlaGln

CGTCCCGTTTCACTC CTTGCCAGCCCCTGG ACATCACCCACTTGG CTCAAGACCAATGGA     720
    ArgProValSerLeu LeuAlaSerProTrp ThrSerProThrTrp LeuLysThrAsnGly
```

Mutations made to the Gcc insert are underlined

GCGGTGAATGGGAAG GGGTCACTCAAGGGA CAGCCCGGAGACATC TACCACCAGACCTGG    780
      AlaValAsnGlyLys GlySerLeuLysGly GlnProGlyAspIle TyrHisGlnThrTrp

GCCAGATACTTTGTG AAGTTCCTGGATGCC TATGCTGAGCACAAG TTACAGTTCTGGGCA    840
      AlaArgTyrPheVal LysPheLeuAspAla TyrAlaGluHisLys LeuGlnPheTrpAla

GTGACAGCTGAAAAT GAGCCTTCTGCTGGG CTGTTGAGTGGATAC CCCTTCCAGTGCCTG    900
      ValThrAlaGluAsn GluProSerAlaGly LeuLeuSerGlyTyr ProPheGlnCysLeu

GGCTTCACCCCTGAA CATCAGCGAGACTTA ATTGCCCGTGACCTA GGTCCTACCCTCGCC    960
      GlyPheThrProGlu HisGlnArgAspLeu IleAlaArgAspLeu GlyProThrLeuAla

AACAGTACTCACCAC AATGTCCGCCTACTC ATGCTGGATGACCAA CGCTTGCTGCTGCCC   1020
      AsnSerThrHisHis AsnValArgLeuLeu MetLeuAspAspGln ArgLeuLeuLeuPro

CACTGGGCAAAGGTG GTACTGACAGACCCA GAAGCAGCTAAATAT GTTCATGGCATTGCT   1080
      HisTrpAlaLysVal ValLeuThrAspPro GluAlaAlaLysTyr ValHisGlyIleAla

GTACATTGGTACCTG GACTTTCTGGCTCCA GCCAAAGCCACCCTA GGGGAGACACACCGC   1140
      ValHisTrpTyrLeu AspPheLeuAlaPro AlaLysAlaThrLeu GlyGluThrHisArg

CTGTTCCCCAACACC ATGCTCTTTGCCTCA GAGGCCTGTGTGGGC TCCAAGTTCTGGGAG   1200
      LeuPheProAsnThr MetLeuPheAlaSer GluAlaCysValGly SerLysPheTrpGlu

CAGAGTGTGCGGCTA GGCTCCTGGGATCGA GGGATGCAGTACAGC CACAGCATCATCACG   1260
      GlnSerValArgLeu GlySerTrpAspArg GlyMetGlnTyrSer HisSerIleIleThr

AACCTCCTGTACCAT GTGGTCGGCTGGACC GACTGGAACCTTGCC CTGAACCCCGAAGGA   1320
      AsnLeuLeuTyrHis ValValGlyTrpThr AspTrpAsnLeuAla LeuAsnProGluGly

GGACCCAATTGGGTG CGTAACTTTGTCGAC AGTCCCATCATTGTA GACATCACCAAGGAC   1380
      GlyProAsnTrpVal ArgAsnPheValAsp SerProIleIleVal AspIleThrLysAsp

ACGTTTTACAAACAG CCCATGTTCTACCAC CTTGGCCATTTCAGC AAGTTCATTCCTGAG   1440
      ThrPheTyrLysGln ProMetPheTyrHis LeuGlyHisPheSer LysPheIleProGlu
```

Mutations made to the Gcc insert are underlined

GGCTCCCAGAGAGTG GGGCTGGTTGCCAGT CAGAAGAACGACCTG GACGCAGTGGCATTG   1500
GlySerGlnArgVal GlyLeuValAlaSer GlnLysAsnAspLeu AspAlaValAlaLeu

ATGCATCCCGATGGC TCTGCTGTTGTGGTC GTGCTAAACCGCTCC TCTAAGGATGTGCCT   1560
MetHisProAspGly SerAlaValValVal ValLeuAsnArgSer SerLysAspValPro

CTTACCATCAAGGAT CCTGCTGTGGGCTTC CTGGAGACAATCTCA CCTGGCTACTCCATT   1620
LeuThrIleLysAsp ProAlaValGlyPhe LeuGluThrIleSer ProGlyTyrSerIle

CACACCTACCTGTGG CATCGCCAGTGATGG AGCAGATACTCAAGG AGGCACTGGGCTCAG   1680
HisThrTyrLeuTrp HisArgGln

NotI
CCTGGGCATTAAAGG GACAGAGTCAGCGAA TTCTGCAGATATCCA TCACACTGGCGGCCG   1740

C                                                                 1741
```

Mutations made to the Gcc insert are underlined

Fig. 5C ured natural ## PRODUCTS AND METHODS FOR GAUCHER DISEASE THERAPY

CROSS REFERENCE TO RELATED APPLICATIONS

This application claims priority to Canadian Application No. 2,272,055, filed Jun. 2, 1999, and to U.S. provisional Application No. 60/137,598, filed Jun. 3, 1999.

FIELD OF THE INVENTION

The invention relates to products and methods for medical treatment of Gaucher disease and, in particular, nucleic acid molecules, polypeptides and vectors for polypeptide or gene therapy treatment.

BACKGROUND OF THE INVENTION

Gaucher disease is a lysosomal storage disease caused by the deficiency of functional glucocerebrosidase (Gcc) enzyme. Gcc is present in all cell types. The defective enzyme cannot break down a fatty substance, glucocerebroside, which is an important component of cell membranes. The fat accumulates in macrophages (which are known as the "Gaucher cells"). The fat-laden macrophages are found typically in the liver, spleen, bone marrow and lungs. The amount of the enzyme deficiency varies from person to person as do the symptoms. Some patients may show no clinical symptoms, while others may die from the disease. The symptoms of the disease and mutant forms of Gcc that cause Gaucher disease are described, for example, in U.S. Pat. No. 5,266,459 (Beutler) and U.S. Pat. No. 5,234,811 (Beutler and Sorge).

There are therapies for Gaucher disease. Ceredase is a form of the Gcc enzyme from placenta that is able to metabolize the fat in Gaucher cells. The enzyme restores normal function to a Gaucher cell. The amount of enzyme used in treatment varies. As much as 30–60 units per kilogram of bodyweight (U/kg/bw) may be given every other week. Positive results have been reported with 2.3 U/kg/bw given three times a week. Lower doses, such as 1–5 U/kg/bw twice weekly, have also been used with success, but this is less frequent. The intarcellular half life of the enzyme is up to 60 hours. A large number of placentas are needed to make sufficient Ceredase, so this form of therapy is very expensive. It has been almost completely replaced by treatment with a recombinant form of the enzyme, Cerezyme but this therapy is also expensive. Cerezyme is dispensed as a powder whereas Ceredase comes as a liquid. Sterile water must be added to the Cerezyme bottle to dissolve the powder. The shelf life of the drugs is short (<3 months), and splitting doses is cumbersome and wasteful. Allergic reactions to Ceredase are common, but rarely life-threatening. Adverse reactions to Cerezyme appear to be less common, but experience with the drug is still very limited.

Gcc has been structurally modified in order to obtain improved pharmacokinetics over naturally occurring Gcc (which is derived from placenta). These modifications include amino acid modifications as well as carbohydrate changes. For example, U.S. Pat. No. 5,549,892 discloses a recombinant polypeptide that differs from naturally occurring Gcc by the presence of histidine in place of arginine at position 495. In another embodiment, the carbohydrate remodeled recombinant Gcc has increased fucose and N-acetyl glucosamine residues compared to remodeled naturally occurring Gcc. The increased pharmacokinetics of these compounds provides a therapeutic effect at doses that are lower than those required using remodeled, naturally occurring Gcc. However, this Gcc remains expensive to provide. Furthermore, improved pharmacokinetics does not necessarily compensate for inadequate bioavailability of Gcc.

Gene therapy has been administered to Gaucher patients. All experiments carried out to date have been undertaken using ex vivo, retrovirus-mediated transfection, which requires sophisticated laboratory facilities and is very expensive. Although transgene expression could be demonstrated in mice undergoing this procedure, experiments in humans have been disappointing. No clinically significant Gcc gene expression has been reported in humans undergoing retrovirus-mediated transfection with existing Gcc gene preparations. One problem of gene therapy is in reproducibly obtaining high-level, tissue-specific and enduring expression from genes transferred into cells. Currently, there is no suitable gene therapy vector that expresses at a high level for Gaucher disease gene therapy.

SUMMARY OF THE INVENTION

The invention includes a modified Gcc cDNA insert that can be inserted into any mammalian expression vector for use in the medical treatment of Gaucher disease. In a preferred embodiment, the modified cDNA was inserted into a vector named pINEX2.0 which was then used to transfect mammalian cells. When pINEX2.0 containing the unmodified Gcc cDNA coding sequence, pINEX5'GCC3', was transfected into cells, their RNA purified from cell lysates and subjected to reverse transcription followed by the polymerase chain reaction (RT-PCR), two distinct major bands were observed after agarose gel electrophoresis (FIG. 1). Isolation, purification and sequencing of the RT-PCR products identified a major aberrantly spliced mRNA species which encodes only a 19 amino acid peptide before encountering a STOP codon. Surprisingly, this aberrant splicing event occurred completely within the Gcc cDNA coding sequence (FIG. 2), i.e. no vector sequences were involved. Site directed mutagenesis was performed to modify the nucleotide sequence in the region of aberrant mRNA splicing without affecting polypeptide coding (FIG. 3; SEQ ID NOS.: 2, 4, and 6). Modifications were aimed at disrupting the known consensus sequences for RNA-splicing (Krawczak et al. 1992). The effectiveness of these modifications were tested by transient transfection into CHO cells, followed by our human-specific immunoprecipitation assay for Gcc. Data (n=18) indicate a 5±1 (Std. Error)-fold increase in Gcc activity was achieved when the modified replaced the unmodified insert in the pINEX2.0 expression vector.

The invention relates to an isolated Gcc DNA molecule, wherein the DNA molecule has a modification in at least one nucleotide that disrupts a splicing consensus sequence and prevents splicing of mRNA produced from the DNA molecule, while preserving the ability of the DNA to express active Gcc. The modification impairs a consensus nucleotide sequence needed to induce splicing. The DNA molecule is preferably modified at two cryptic splice sites. The DNA preferably includes a mutation in the 3' junction site. In one embodiment, the mutation is as shown in the 3' junction site (SEQ ID NO.: 18) in Table 1, or a functionally equivalent mutation. In another embodiment, the DNA molecule includes a mutation in the 5' splice junction site. The mutation is preferably as shown in the 5' junction site (SEQ ID NO.: 19) in Table 1, or a functionally equivalent mutation.

The DNA molecule preferably includes all or part of the nucleotide sequence shown in FIG. 5 (SEQ ID NO.: 13).

Another aspect of the invention relates to a vector including a DNA molecule of the invention. The vector preferably includes a promoter that is functional in a mammalian cell.

The invention also includes mRNA produced from the DNA molecule or vector of the invention.

Another aspect of the invention relates to a method of medical treatment of Gaucher disease in a mammal, including administering to the mammal an effective amount of a nucleic acid molecule of the invention or a vector of the invention and expressing an effective amount of the polypeptide encoded by the nucleic acid molecule for alleviating clinical symptoms of Gaucher disease.

The invention includes a host cell, or progeny thereof, including a nucleic acid molecule of the invention. The host cell is preferably selected from the group consisting of a mammalian cell, a human cell and a Chinese Hamster Ovary cell. The invention also includes a method for producing a recombinant host cell capable of expressing a Gcc nucleic acid molecule, the method including introducing into the host cell a vector of the invention. The invention also includes a method for expressing a Gcc polypeptide in a host cell including culturing the host cell under conditions suitable for DNA molecule expression. Another aspect of the invention relates to a method for producing a transgenic cell that expresses elevated levels of Gcc polypeptide relative to a non-transgenic cell, including transforming a cell with a vector of the invention.

The invention includes an isolated polypeptide encoded by and/or produced from a nucleic acid molecule of the invention, or a vector of the invention.

The invention includes a method of producing a genetically transformed cell which expresses or overexpresses a Gcc polypeptide, including: a) preparing a Gcc nucleic acid molecule according to any of claims 1–18; b) inserting the nucleic acid molecule in a vector so that the nucleic acid molecule is operably linked to a promoter; c) inserting the vector into a cell. The invention includes a transgenic cell produced according to the method of the invention.

The invention also includes a pharmaceutical composition, including a carrier and (i) a nucleic acid molecule of the invention (ii) a vector of the invention or (iii) Gcc polypeptide produced from (i) or (ii), in an effective amount for reducing clinical symptoms of Gaucher disease. The carrier preferably carrier includes a liposome.

BRIEF DESCRIPTION OF THE DRAWINGS

Preferred embodiments of the invention will be described in relation to the drawings in which:

FIG. 3. (SEQ ID NOS.: 2, 4, and 6). Comparison of consensus splice site donor/acceptor site and "Cryptic" splice sites in Gcc cDNA. Sequences of (a) unmodified Gcc cDNA contained in pINEX5'Gcc3' (b) In a preferred embodiment, this sequence represents modified Gcc cDNA contained in pINEX-WEIRD. The translated amino acid sequence for either the modified or unmodified Gcc cDNAs is also given, note that the modified nucleotides had no effect on the amino acid sequence.

FIG. 4. (SEQ ID NOS.: 11 and 12) The sequences of the aberrantly processed transcript from the unmodified Gcc cDNA insert in pINEX5'Gcc3' and its translated polypeptide.

FIG. 5 (SEQ ID NOS.: 13 and 14) Modified DNA and its translated polypeptide. In a preferred embodiment, this sequence represents modified Gcc cDNA.

DETAILED DESCRIPTION OF THE INVENTION

The invention satisfies the need for a DNA (preferably a cDNA) that when inserted into any mammalian expression vector transcribes RNA that is resistant to aberrant processing in the transfected or transduced target cells and thus, is much more likely to translate the functional full length Gcc protein. Therefore, such a modified insert would improve the levels of Gcc expression when used in any vectors designed for in vivo or ex vivo gene therapy treatments of Gaucher disease. As well, when inserted into any efficient mammalian expression vector, such as pINEX2.0, the modified Gcc cDNA as compared to the unmodified cDNA will increase the production levels of recombinate Gcc polypeptide for use in enzyme replacement therapy for Gaucher disease. Thus, the modified insert directs a higher level of Gcc expression through a mechanism that is independent of the mammalian expression vector used whether in vivo or in vitro. The modified insert is safe as preferably no change in the amino acid sequence of Gcc is encoded by the nucleotide changes, and should confer a sustained and appropriate level of cell-specific expression for gene therapy when coupled with the appropriate vector and transfection or transduction methodologies. The expressed DNA insert is preferably a modified Gcc cDNA or a modified fragment of a Gcc cDNA that express a polypeptide having Gcc activity which is effective for treatment of Gaucher disease. The DNA is modified to prevent aberrant cellular splicing of its mRNA produced when expressed in mammalian cells. The modified DNA insert may be used with any expression vector to transfect or transduce any mammalian cell type, such as CHO cells for the expression of human Gcc for enzyme replacement. These would also include human stem cells for ex vivo gene therapy or macrophages for in vivo gene therapy.

The invention also includes the methods of making the modified DNA. The methods may be applied to a Gcc DNA from any source that requires modification to avoid undesirable splicing including humans, other mammals or synthetic DNA.

Figure 1:
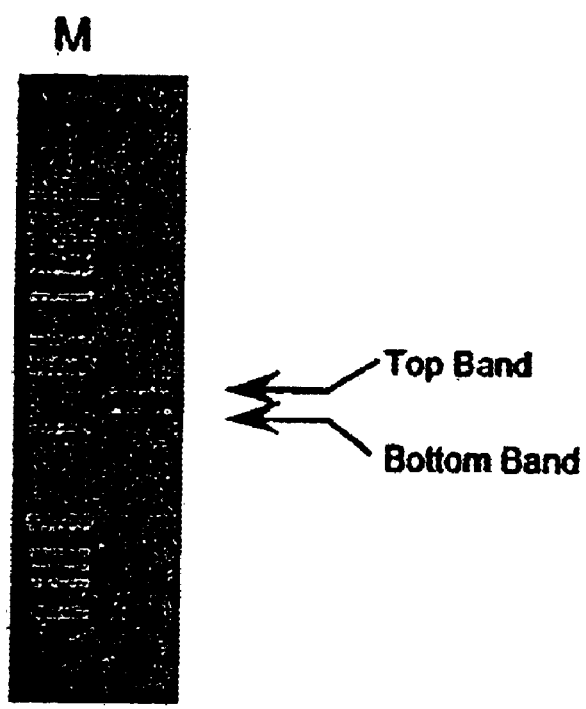
FIG. 1. Separation of RT-PCR products from CHO cell permanently transfected with pINEX-5'-GCC-3'.
Figure 2:
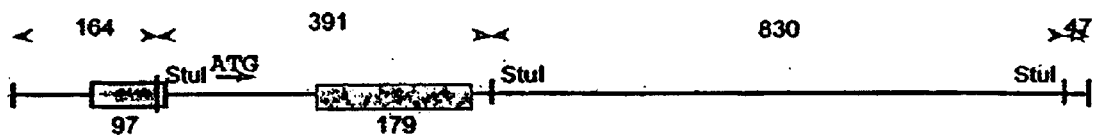
FIG. 2. Diagrammatic Representation of possible RT-PCR products representing mRNA splice variants from pINEX-5'-GCC-3'.
Figure 2:
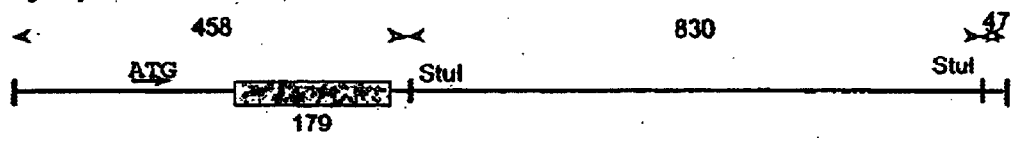
Figure 2:
Figure 2:

During the search to improve the efficiency of human Gcc expression it was determined that a major amount of the RNA transcribed from any vector was aberrantly spliced due to cryptic 5' and 3' splice sites contained in the human Gcc cDNA (FIGS. 1 & 2). Since this RNA species encodes only a 19 amino acid peptide, it is far less stable than the properly spliced product encoding the complete 536 residues of Gcc (Maquat 1996), and therefore transcribed at a much higher level than is indicated from our steady-state RT-PCR data (FIG. 1). We modified the two cryptic sites in a manner that conserved the wild type amino acid sequence while destroying the consensus nucleotide sequences needed to induce splicing (FIG. 3; SEQ ID NOS.: 2, 4, and 6). Transient expression of this modified insert indicated a 5-fold increase in Gcc expression. Such an increase in expression efficiency is not only valuable for any gene therapy approach, but also useful in decreasing the cost of enzyme replacement since the enzyme source is now Gcc-transfected mammalian cells.

Treatment using any vector containing a modified insert to prevent aberrant transcript processing (by gene therapy or by administration of polypeptide produced from a vector) will lower the cost of the present enzyme replacement therapy (currently as much as about US$100,000 per yr. for a patient) by increasing the yield of functional Gcc protein.

The modified insert when used with any appropriate expression vector is also used to direct the expression of Gcc for use in research and characterization of the enzyme's function.

Other useful DNA inserts include a nucleic acid molecule having at least about: 50%, 60%, 70%, 80%, 90%, 95%, 99% or 99.5% sequence identity to the modified Gcc nucleic acid molecule (the Gcc sequence in FIG. 4(b) (SEQ ID NO.: 13)) wherein the molecule having sequence identity has a modification in at least one nucleotide (preferably two nucleotides) that disrupts a splicing consensus sequence and prevents splicing of mRNA while it encodes a polypeptide having Gcc activity. Changes in the Gcc nucleotide sequence which result in production of a chemically equivalent (for example, as a result of redundancy of the genetic code) or chemically similar amino acid (for example where sequence similarity is present), may also be made to produce high levels of unspliced transcript from the Gcc cDNA for therapeutic use. The DNA molecule or DNA molecule fragment may be isolated from a native source (in sense or antisense orientations) and modified or synthesized (with or without subsequent modification). It may be a mutated native or synthetic sequence or a combination of these in order to prevent or decrease aberrantly spliced transcripts.

Selection of Vector

Separating the Gcc activity derived from transfected human cDNA from the endogenous Gcc activity of the host cells, e.g. CHO, was done to determine the efficiency of expression vectors. A high level of expression is needed not only for any in vivo or ex vivo gene therapy approach, but also for the efficiency of producing Gcc for enzyme replacement therapy now being done in transfected cells (Grabowski et al. 1995). We have developed an immunoprecipitation assay that is specific for the human enzyme and have used it to evaluate several expression vectors. The vector producing the highest level of Gcc in transiently transfected CHO cells was pINEX2.0 from INEX Pharmaceuticals. The vector contains a CMV-based promoter and a potential intron prior to the initiating ATG of the Gcc cDNA. In general our results indicated that a CMV-based promoter gave the highest level of expression and that the placement of the vector's intron at the 5' end of the insert was superior to placing it at the 3' end. Other suitable vectors will be apparent to a skilled person.

After some initial modifications to the 5' untranslated end of the cDNA construct to ensure a match with the consensus sequences for protein initiation (Kozak 1987) and the 3' end to eliminate most of the untranslated nucleotides prior to the vector's polyadenylation signal, a lysate from transiently transfected CHO cells still produced low levels of Gcc specific activity, requiring our immunoprecipitation assay to detect the increase in human activity in the cells' total Gcc pool. A line of permanently-transfected CHO cells was prepared in order to analyzed the sequence(s) of the Gcc mRNA(s) being transcribed from the expression vector.

IDENTIFICATION AND CHARACTERIZATION OF DIFFERENTIALLY SPLICED RNA

Cells Expressing Differentially Spliced RNA

A CHO cell line was permanently co-transfected with the pINEX-5'-GCC-3' construct and a construct containing a selectable marker, pREP10. After selection and isolation of individual clones, the clones were assayed to determine specific activity of Gcc (in nmole/hr/mg total lysate protein). One clone, termed A7, was grown in larger scale and RNA isolated from it. A reverse transcription reaction followed by PCR, RT-PCR, was performed on total cellular RNA from CHO control cells and A7 clone cells. Following agarose gel electrophoresis, two major bands were observed (see FIG. 1).

Restriction Digest Analysis

The major bands of the RT-PCR reaction were electrophoretically separated on a larger scale and the band(s) excised. The purified cDNA was ligated into the pCR2.1 cloning vector. Restriction digest analysis of the clones obtained using Stu I and Eco RI, revealed a series of different patterns, consistent with possible aberrant splicing (data not shown).

Sequencing Analysis

Sequencing of representative clones of each pattern, obtained from the high- and/or low-molecular weight bands, revealed a number of differentially spliced products. In the high-molecular weight band, 5 out of 10 clones contained product that was spliced at the upstream site in the vector only, producing wild-type message. One out of 10 contained a completely unspliced product, and another 1 out of 10 contained a product with a restriction map consistent with both upstream (vector) and downstream (insert) splice events taking place (FIG. 2). Remaining clones contained unidentifiable restriction maps and were therefore not sequenced. Sequencing and restriction digest analysis of the low-molecular weight band revealed that in 7 of 10 clones both splices had taken place, and in 2 out of 10 only the upstream splice event (wild-type message) had occurred.

Sequencing results confirmed that the major alternatively spliced species resulted from the removal of sequences within the Gcc cDNA itself, through the recognition of cryptic 5' and 3' splice sites roughly corresponding to the known consensus sequences that induce RNA splicing in mammalian cells (Krawczak et al. 1992). The deduced amino acid sequence from this RNA species predicts a reading frame shift after $Arg^{17}$ and an early stop two codons later (FIG. 3; SEQ ID NOS.: 2, 4, and 6). This would encode only a 19 amino acid peptide lacking even a complete signal sequence, necessary for targeting the protein to the cell's endoplasmic reticulum. In order to eliminate aberrant splicing, the Gcc cDNA was modified by site-directed mutagenesis to alter some of the critical nucleotides making up the consensus sequences (Krawczak et al. 1992) to ensure that the cryptic splice sites no longer be recognized by the RNA processing mechanism. Care was taken to preserve the amino acid coding sequence. FIG. 3 (SEQ ID NOS.: 2, 4, and 6) shows the consensus sequence for the 5' or 3' splice junctions (Krawczak et al. 1992), the original nucleotide sequence of the Gcc cDNA, the deduced amino acid sequence, and the modifications undertaken to destroy the consensus splicing sequences. Other modifications to destroy the consensus splicing sequences will be apparent.

Transfection Experiments

Eighteen independent transient transfection experiments were performed to compare Gcc expression levels between pINEX-5'-GCC-3' to pINEX-WEIRD. After correcting for transfection efficiency with 1-galactosidase (see Methods), pINEX-WEIRD produced 5±1 (standard error) fold higher levels of Gcc activity (see example in Table 2).

Future work will confirm that all aberrent processing of the Gcc transcript from the modified Gcc cDNA is eliminated. If not, other modifications based on the known consensus splice-sites sequences will be undertaken.

Modified DNA/DNA Having Sequence Identity

Many modifications may be made to the vector and Gcc DNA sequences and these will be apparent to one skilled in the art. The invention includes nucleotide modifications of the sequences disclosed in this application (or fragments thereof) that are capable of expressing Gcc in in vivo or in vitro cells. For example, the regulatory sequences may be modified or a nucleic acid sequence to be expressed may be modified using techniques known in the art. Modifications include substitution, insertion or deletion of nucleotides or altering the relative positions or order of nucleotides. The invention includes DNA which has a sequence with sufficient identity to a nucleotide sequence described in this application to hybridize under moderate to high stringency hybridization conditions. Hybridization techniques are well known in the art (see Sambrook et al. Molecular Cloning: A Laboratory Manual, Most Recent Edition, Cold Spring Harbor Laboratory Press, Cold Spring Harbor, N.Y.). High stringency washes have low salt (preferably about 0.2% SSC), and low stringency washes have high salt (preferably about 2% SSC). A temperature of about 37° C. or about 42° C. is considered low stringency, and a temperature of about 50–65° C. is high stringency. The modified inserts encoding Gcc of the invention also include DNA molecules (or a fragment thereof) having at least 50% identity, at least 70% identity, at least 80% identity, at least 90% identity, at least 95% identity, at least 96% identity, at least 97% identity, at least 98% identity or, most preferred, at least 99%, 99.5% or 99.8% identity to a modified Gcc nucleic acid molecule acid as shown in FIG. 4 (SEQ ID NO.: 11), which have a modified consensus sequence to prevent splicing and which are capable of expressing DNA molecules in vivo or in vitro. Identity refers to the similarity of two nucleotide sequences that are aligned so that the highest order match is obtained. Identity is calculated according to methods known in the art. For example, if a nucleotide sequence (called "Sequence A") has 90% identity to the Gcc sequence in FIG. 5 (SEQ ID NO.: 13)], then Sequence A will be identical to the referenced portion of FIG. 5 (SEQ ID NO.: 13) except that Sequence A may include up to 10 point mutations (such as deletions or substitutions with other nucleotides) per each 100 nucleotides of the referenced portion of FIG. 5 (SEQ ID NO.: 13). The invention also includes DNA sequences which are complementary to the aforementioned sequences. "Sequence identity" may be determined, for example, by the Gap program. The algorithm of Needleman and Wunsch (1970 J Mol. Biol. 48:443–453) is used in the Gap program.

The DNA has a modification in at least one nucleotide that disrupts a splicing consensus sequence and prevents splicing of mRNA while it encodes a polypeptide having Gcc activity. This means an enzyme that can both convert the natural substrate, glucocerebroside (D-glucosylceramide), to ceramide and glucose under the appropriate conditions, and also hydrolyzed an artificial substrate, 4-methylumbelliferyl-β-D-glucopyranoside, at a rate of greater than 10 μmoles/hr/mg of purified Gcc polypeptide.

Functionally Equivalent Nucleic Acid Molecules Identified by Hybridization

Other functionally equivalent forms of the modified Gcc DNA of the invention can be identified using conventional DNA-DNA or DNA-RNA hybridization techniques. Thus, the present invention also includes nucleotide sequences that hybridize to the sequence in FIG. 5 (SEQ ID NO.: 13) or its complementary sequence, wherein the molecule that hybridizes to the Gcc portion in FIG. 5 (SEQ ID NO.: 13) has a modification in at least one nucleotide (more preferably at least two nucleotides) that disrupts a splicing consensus sequence and prevents aberrant splicing of MRNA while it encodes a polypeptide having Gcc activity. Such nucleic acid molecules preferably hybridize to the Gcc sequence in FIG. 5 (SEQ ID NO.: 13) under moderate to high stringency conditions. For example, high stringency washes have low salt (preferably about 0.2% SSC), and low stringency washes have high salt (preferably about 2% SSC). A temperature of about 37° C. or about 42° C. is considered low stringency, and a temperature of about 50–65° C. is high stringency (see Sambrook et al. Molecular Cloning: A Laboratory Manual, Most Recent Edition, Cold Spring Harbor Laboratory Press, Cold Spring Harbor, N.Y.).

A nucleic acid molecule is considered to be functionally equivalent to the modified Gcc nucleic acid molecules of the present invention if the nucleic acid molecule has a modification in at least one nucleotide that disrupts a splicing consensus sequence and prevents splicing of mRNA while it encodes a polypeptide having Gcc activity (Gcc activity means an enzyme that can both convert the natural substrate, glucocerebroside (D-glucosylceramide), to ceramide and glucose under the appropriate conditions, and also hydrolyzed an artificial substrate, 4-methylumbelliferyl-β-D-glucopyranoside, at a rate of greater than 10 μmoles/hr/mg of purified Gcc polypeptide).

Cells Containing a Vector of the Invention

The invention relates to a host cell (isolated cell in vitro or a cell in vivo, or a cell treated ex vivo and returned to an in vivo site) containing a vector and modified Gcc sequence of the invention. The preparation of transformed cells is done according to known techniques (see Materials and Methods for example of CHO cells containing a vector). The invention includes methods of expressing Gcc in the cell.

Pharmaceutical Compositions

The pharmaceutical compositions of this invention used to treat patients having Gaucher Disease could include an acceptable carrier, auxiliary or excipient. Polypeptides may be administered in pharmaceutical compositions in enzyme replacement therapy or in gene therapy.

The pharmaceutical compositions can be administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (MV) vectors. Dosages to be administered depend on patient needs, on the desired effect and on the chosen route of administration. The vectors may be introduced into the cells or their precursors using in vivo delivery vehicles such as liposomes or DNA or RNA virus vectors. They may also be introduced into these cells using physical techniques such as microinjection or chemical methods such as coprecipitation. The vector may be introduced into any mammalian cell type, such as CHO cells or human cells.

The pharmaceutical compositions can be prepared by known methods for the preparation of pharmaceutically acceptable compositions which can be administered to patients, and such that an effective quantity of the vector or polypeptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA).

On this basis, the pharmaceutical compositions could include an active compound or substance, such as a polypeptide, in association with one or more pharmaceutically acceptable vehicles or diluents, and contained in buffered solutions with a suitable pH and isoosmotic with the physiological fluids. The methods of combining the vectors with the vehicles or combining them with diluents is well known to those skilled in the art. The composition could include a targeting agent for the transport of the active compound to specified sites within the mammalian cells.

Method of Medical Treatment of Gaucher Disease

Any vectors containing the DNA molecules of the invention may be administered to mammals, preferably humans, in gene therapy using techniques described below. The polypeptide produced from the modified inserts may also be administered to mammals, preferably humans, in enzyme replacement therapy.

Gene Therapy

Gene therapy to replace Gcc expression (Nolta et al. 1992; Tsai et al. 1992; Sidransky et al. 1993; Schuening et al. 1997; Dunbar et al. 1998) may be useful to modify the development or progression of Gaucher disease. The invention includes methods for providing gene therapy for treatment of diseases, disorders or abnormal physical states characterized by insufficient Gcc expression or inadequate levels or activity of Gcc polypeptide.

The invention includes methods and compositions for providing a nucleotide sequence encoding Gcc or biologically functional equivalent nucleotide sequence to the cells of an individual such that expression of Gcc in the cells provides the biological activity or phenotype of Gcc polypeptide to those cells. Sufficient amounts of the nucleotide sequence are administered and expressed at sufficient levels to provide the biological activity or phenotype of Gcc polypeptide to the cells. For example, the method can involve a method of delivering a gene encoding Gcc to the cells of an individual having a disease, disorder or abnormal physical state, comprising administering to the individual a vector comprising DNA encoding Gcc wherein the DNA has modified sites to prevent undesirable splicing. The method may also relate to a method for providing an individual having a disease, disorder or abnormal physical state with biologically active Gcc polypeptide by administering DNA encoding Gcc. The method may be performed ex vivo or in vivo. Gene therapy methods and compositions are demonstrated, for example, in U.S. Pat. Nos. 5,672,344, 5,645,829, 5,741,486, 5,656,465, 5,547,932, 5,529,774, 5,436,146, 5,399,346 and 5,670,488, 5,240,846.

The method also relates to a method for producing a stock of recombinant virus by producing virus suitable for gene therapy comprising modified DNA encoding Gcc. This method preferably involves transfecting cells permissive for virus replication (the virus containing modified Gcc) and collecting the virus produced.

Typically, a male or female is treated with the vector containing the invention (subject age will typically range from 1 to 60 years of age). At the time of treatment, he typically will have bone involvement, bone thinning and bone pain and will have an enlarged spleen and liver. The vector containing the invention is administered intravenously in order to achieve a desired level of enzyme in the patient. Treatments are repeated as deemed appropriate by a physician to ameliorate the clinical symptoms of Gaucher disease. Such treatments may be life-long.

Patients report significant improvement in bone involvement, pain and thinning, with reduction in frequency and/or intensity of pain episodes, or complete disappearance of skeletal pain often within the first six months of treatment. Patients also show improvement in cortical bone thickness. Enlargement of the spleen and liver are reduced. One of the disease markers, the enzyme chitotriosidase, shows a dramatic reduction during the course of a year.

Administration of Gcc Polypeptide

The Gcc polypeptide is administered in pharmaceutical compositions in enzyme replacement therapy, examples of which are described above (Beutler et al. 1991; Barton et al. 1992; Fallet et al. 1992; Brady et al. 1994; Grabowski et al. 1995; Rosenthal et al. 1995).

Typically, a male or female is treated with the polypeptide of the invention (subject age will typically range from 1 to 60 years of age). At the time of treatment, he typically will have bone involvement, bone thinning and bone pain and may have an enlarged spleen and liver. The polypeptide of the invention is administered intravenously at about 30 U/kg every 2 weeks in order to achieve a desired level of enzyme in the patient.

Patients report significant improvement in bone involvement, pain and thinning, with reduction in frequency and/or intensity of pain episodes, or complete disappearance of skeletal pain often within the first six months of treatment. Patients also show improvement in cortical bone thickness. Enlargement of the spleen and liver are reduced. One of the disease markers, the enzyme chitotriosidase, shows a dramatic reduction during the course of a year.

Research Tool

Mammals and cell cultures transfected or transduced with vectors containing the invention are useful as research tools. Mammals and cell cultures are used in research according to numerous techniques known in the art. For example, one may obtain cells or mice (Tybulewicz et al. 1992) that express low levels of the normal or mutant Gcc polypeptide and use them in experiments to assess expression of a recombinant Gcc nucleotide sequence. In an example of such a procedure, experimental groups of mice are transformed with vectors containing recombinant Gcc genes to assess the levels of polypeptide produced, its functionality and the phenotype of the cells or mice (for example, physical characteristics of the cell structure). Some of the changes described above to optimize expression may be omitted if a lower level of expression is desired. It would be obvious to one skilled in the art that changes could be made to alter the levels of polypeptide expression.

In another example, a cell line (either an immortalized cell culture or a stem cell culture) is transformed with a DNA molecule of the invention (or variants) to measure levels of expression of the DNA molecule and the activity of the DNA molecule. For example, one may obtain mouse or human cell lines or cultures bearing the vector of the invention and obtain expression after the transfer of the cells into immunocompromised mice.

Using Exogenous Agents in Combination With the Hybrid Gene

Cells transfected or transduced with a DNA molecule or polypeptide according to the invention may, in appropriate circumstances, be treated with conventional medical treatment of Gaucher disease, such as enzyme replacement therapy. The appropriate combination of treatments would be apparent to a skilled physician.

Material and Methods

Reagents:

All reagents used during the course of these experiments were of research grade or molecular biology grades, as appropriate. Substrate for the acid 11-glucosidase (Gcc) activity, 4-methylumbelliferyl-β-D-glucopyranoside (MUGc), was purchased from Sigma and purified additionally as described below. Oligonucleotide primers were obtained, as a lyophilized powder, from the Hospital for Sick Children Biotechnology Service Centre's DNA Synthesis Service. Tissue culture media (alpha-MEM) was obtained from the University of Toronto Media Preparation Service. Fetal bovine serum were obtained from CanSera through the Hospital for Sick Children Tissue Culture Service.

Lac Z. Neutral β-Galactosidase Assay

Samples of cell lysates were diluted into water to a final volume of 60 μL. Substrate solution (190 μL), prepared by dissolving 19 mg of 4-MU-β-gal (4-methylumbelliferyl-β-galactoside) in 100 ml of pH 7.0 0.1M citrate buffer, was added. The mixture was incubated at 37° C. for 30 minutes and then stopped by the addition of 2.0 ml of 0.1 M MAP. Fluorescence of standard quantities of free 4-MU in 0.1 MAP (2-methyl-2-amino-1-propanol) and the assay mixtures were determined on a fluorescence spectrophotometer using 365 nm excitation and 450 nm emission wavelengths. Polypeptide concentration of the cell lysates were determined by the Bio-Rad method. Specific activity of the lysates were determined as nmole MU/mg polypeptide.

Acid β-Glucosidase (Gcc) Activity (Specific or Total):

Samples were prepared by freeze-thaw lysis (5×) in PBS containing 0.1% sodium taurocholate (NaTC), usually 100 μL for a P100 dish of confluent CHO cells. A sample of the lysate (5–20 μL) was diluted with 0.25% BSA to a total volume of 100 μL. Reagents were added in the following order: citrate/phosphate buffer (1M/2M, pH 4.5), 25 μL; 2% NaTC in ddH$_2$O, 25 μL; and 20 mM of the MUGc substratesolution, 100 μL. The reaction was typically allowed to proceed for 1 hour at 37° C. and then stopped by the addition of 3.0 ml of 0.1M MAP, pH 10.5. Fluorescence of the released 4-MU was measured with the use of on a Perkin Elmer LS 30 Luminescence Spectrometer with sipper attachment. Polypeptide content was determined using the BioRad Protein Assay reagent.

Substrate solution (20 mM) was prepared by dissolving MUGc in ddH$_2$O and heating to 40–50° C. for 15–20 minutes with occasional agitation. The solution was cooled and then extracted 3× with an equal volume of ethyl acetate. The final aqueous solution was bubbled with N$_2$ gas (to remove residual ethyl acetate) and aliquoted into tubes which were then frozen and stored at −20° C. until needed. The substrate solution was thawed for use in a beaker of warm water, then vortexed vigorously to ensure complete dissolution of any solid material.

Immunoprecipitation Assay:

For each immunoprecipitation assay, 125 μL of Goat anti-rabbit IgG coated magnetic beads (hereafter called "beads") were isolated from suspension using a permanent magnet stand (Advanced Magnetics). Beads were washed 3 times with phosphate-buffered saline containing 0.05% bovine serum albumin (PBS/BSA) by resuspension, and removal from suspension using a magnetic stand, followed by removal of the supernatant. After the final wash the beads were resuspended in 100 μL of PBS/BSA and an appropriate amount of the rabbit anti-Gcc IgG (#5470), usually 4 μg per assay, was added. The mixture was placed in an appropriately sized tube, depending on volume, and allowed to incubate with rotation for 4 hours at 4° C. The bead-antibody complex was precipitated with the permanent magnet stand and washed 3 times with PBS/BSA to remove any remaining free antibody and finally resuspended in 100 μL of PBS/BSA. Cell lysates were prepared as above and diluted into a minimum of 400 μL (to allow for adequate mixing). The washed antibody-bead complex (100 μL) was added to the diluted sample and allowed to incubate overnight at 4° C. with rotation. The samples were placed on ice in the permanent magnet stand and allowed to precipitate for ~30 minutes. The beads in each sample were washed (750 μL) with PBS/BSA containing 0.1% Triton X-100, then twice with PBS/BSA containing 0.2% NaTC. After the final wash, the beads were resuspended in PBS/BSATriton and assayed for Gcc activity (as described above).

Expression of Gcc in Transiently Transfected CHO Cells

CHO cells were co-transfected with either 8 μg of pINEX-5'-GCC-3' or pINEX-WEIRD and 2 μg pCMV-Lac Z (encoding E. coli β-galactosidase as a control for transfection efficiency) using Superfect Reagent (QIAGEN GmBH, Germany), according to the manufacturer's protocol. Cells were harvested after 2 days and the lysates analyzed for Gcc (using the immunoprecipitation assay) and β-galactosidase activity. Final Gcc levels were adjusted based on the relative levels of β-galactosidase activity in each lysate sample.

Cloned CHO Cells Permanently-Transfected with PINEX-5'-GCC-3':

CHO cells were co-transfected with 8 μg of pINEX-5'-GCC-3' and 2 μg pREP10 (containing a hygromycin resistance gene). Selective medium, containing 200 μg/mL hygromycin was added, and the cells were allowed to grow for approximately two weeks, splitting as necessary. After two weeks the cells were harvested by trysinization, counted using a hemocytometer and diluted as necessary to isolate single cells using 96-well dishes. After 10 days, clones that were growing well were transferred into 100 mm dishes and allowed to grow for a further 10 days, splitting as necessary. Cells from each clone were harvested and assayed for Gcc activity. The final clone selected, termed A7, had the highest Gcc activity of all the clones examined.

RNA Isolation and Reverse Transcription and PCR (RT-PCR):

Cells were grown in large dishes (P150), and RNA was isolated from control CHO cells and the A7 clone, according to the one-step guanidinium isothiocyanate procedure (Chomczynski and Sacchi 1987). RNA (1 μg), primer (SPR2 (SEQ ID NO.: 15) (see Table 1), 200 pmol), RNase inhibitor, and ddH$_2$O (to 12.5 μL total), were mixed and incubated at 65° C. for 20 minutes. After cooling on ice for 5 minutes, the remaining components of the RT reaction cocktail were added (RT buffer, DTT, dNTPs, RNase inhibitor, and reverse transcriptase). The reaction cocktail (total 25 μL) was incubated at 37° C. for 90 min.

PCR was performed using the RT reaction products (1 μL) as template. After addition of ddH$_2$O, and primers (SPF (SEQ ID NO.: 16) and 53GCC2000R (SEQ ID NO.: 17) (see Table 1), 20 pmol each), the reaction was incubated at 95° C. for 5 minutes to inactivate the reverse transcriptase. The remaining reaction components (dNTPs, MgCl2, and Taq polymerase (Gibco BRL)) were used at manufacturers suggested levels. Thermocycling was performed under the following conditions: 94° C./3 min; 30 cycles of 94°/1.5 min, 55°/1 min, 72 °/1.5 min; 72°/10 min. Samples of the PCR reaction (10 μL) were loaded onto a 1.5% agarose gel using Tris-Acetate-EDTA buffer (TAE, 40 mM Tris-acetate/2 mM EDTA), electrophoresed and visualized using ethidium bromide.

Cloning of RT-PCR Products:

Electrophoresis of the RT-PCR products from the A7 clone cell line showed two major bands. One full RT-PCR reaction mixture (100 µL) was separated eletrophoretically on an agarose gel, and the two major product bands were excised and purified using the Qiaex II Gel Extraction Kit (QIAGEN GmBH, Germany). The fragments were cloned into the TA cloning vector (pCR2.1) according to the manufacturer's directions (Invitrogen, Carlsbad, Calif.). The inserts were sequenced using either $^{35}$S-T7 Sequencing Kit or $^{33}$P-cycle Sequencing Kit (Amersham Pharmacia Biotech, Sweden) from either the M13 forward or M13 reverse primer location on the vector. Sequencing gels were exposed to BioMaxMR film (Kodak) overnight and subsequently read.

Site-Directed Mutagenesis (Internal "Weird" Spice Fix):

The cryptic splice site located within the Gcc cDNA was modified by site-directed mutagenesis in order to remove potential consensus splice junction sites from the Gcc cDNA. A PCR product was obtained using one oligonucleotide primer which mutagenized a number of bases in the putative 3' junction site (SEQ ID NO.: 18) (3'-junction (see Table 1)) and another for the putative 5'-splice junction site (SEQ ID NO.: 19) (5'-junction (see Table 1)). The PCR reaction contained: 1×Pfu reaction buffer (10× stock provided by manufacturer), 0.4 mM dNTP, 10 ng template DNA (pINEX-5'-GCC-3'), 500 ng of each oligo, and 2.5U Pfu DNA Polymerase in a final volume of 50 µL in the appropriate buffer.

Amplification was performed using a Robocycler 40 Temperature Cycler (Stratagene) for 30 cycles, with temperatures and times as follows: 94° C./45 sec., 59° C./1 min. and 72° C./1 min. 20 sec. The PCR product was used as a mega-primer in the second round of PCR. The second PCR reaction consisted of: 5 µL of the above PCR reaction mixture, 1×Pfu reaction buffer (10× stock provided by manufacturer), 0.4 mM dNTPs, 50 ng template (pINEX-5'-GCC-3'), 500 ng upstream oligo (SPF; SEQ ID NO.: 16) and 5U Pfu DNA polymerase in a final reaction volume of 100 µL. Reaction temperature conditions used were the same as for the initial PCR above. The PCR products were digested with 10U of Dra III and Xho I for 3 hr at 37° C. The plasmid pINEX-5'-GCC-3' was digested in parallel using the same method. Digested products were electrophoretically separated on an agarose gel, and the appropriate pieces were excised and purified as described above. Ligation was performed in a 20 µL final volume using 5U of T4 DNA Ligase (MBI Fermentas, Lithuania), incubating overnight at 16° C. to produce pINEX-WEIRD. DNA was transformed into DH5a E. coli cells (Gibco BRL) and plated onto appropriate LB agar plates containing antibiotics. Plasmid DNA was isolated and screened by restriction digest and sequencing to confirm that they contained the appropriate insert.

The present invention has been described in detail and with particular reference to the preferred embodiments; however, it will be understood by one having ordinary skill in the art that changes can be made thereto without departing from the spirit and scope of the invention.

All publications, patents and patent applications are incorporated by reference in their entirety to the same extent as if each individual publication, patent or patent application was specifically and individually indicated to be incorporated by reference in its entirety.

References

Barton N W, Brady R O, Dambrosia J M, Doppelt S H, Hill S C, Holder C A, Mankin H J, et al (1992) Dose-dependent responses to macrophage-targeted glucocerebrosidase in a child with Gaucher disease. J Pediatr 1:277–280

Beutler E, Kay A C, Saven A, Garver P, Thurston D W, Rosenbloom B E (1991) Enzyme-replacement therapy for Gaucher's disease. N Engl J Med 325:1809–1810

Brady R O, Murray G J, Barton N W (1994) Modifying exogenous glucocerebrosidase for effective replacement therapy in Gaucher disease. J Inherited Metab Dis 17:510–519

Chomczynski P, Sacchi N (1987) Single-step method of RNA isolation by acid guanidinium thiocyanate-phenol-chloroform extraction. Anal. Biochem. 162:156–9

Dunbar C E, Kohn D B, Schiffmann R, Barton N W, Nolta J A, Esplin J A, Pensiero M, et al (1998) Retroviral transfer of the glucocerebrosidase gene into CD34+ cells from patients with Gaucher disease: In vivo detection of transduced cells without myeloablation. Hum Gene Ther 9:2629–2640

Fallet S, Grace M E, Sibille A, Mendelson D S, Shapiro R S, Hermann G, Grabowski G A (1992) Enzyme augmentation in moderate to life-threatening Gaucher disease. Pediatr Res 31:496–502

Grabowski G A, Barton N W, Pastores G, Dambrosia J M, Banerjee T K, McKee M A, Parker C, et al (1995) Enzyme therapy in type 1 Gaucher disease: Comparative efficacy of mannose-terminated glucocerebrosidase from natural and recombinant sources. Ann. Intern. Med. 122:33–39

Kozak M (1987) At least six nucleotides preceding the AUG initiator codon enhance translation in mammalian cells. J. Mol. Biol. 196:947–950

Krawczak M, Reiss J, Cooper D N (1992) The mutational spectrum of single base-pair substitutions in mRNA splice junctions of human genes: causes and consequences. Hum. Genet. 90:41–54

Maquat L E (1996) Defects in RNA splicing and the consequence of shortened translational reading frames. Am. J. Hum. Genet. 59:279–286

Nolta J A, Yu X J, Bahner I, Kohn D B (1992) Retroviral-mediated transfer of the human glucocerebrosidase gene into cultured Gaucher bone marrow. J Clin Invest 90:342–348

Rosenthal D I, Doppelt S H, Mankin H J, Dambrosia J M, Xavier R J, McKusick K A, Rosen B R, et al (1995) Enzyme replacement therapy for Gaucher disease: Skeletal responses to macrophage-targeted glucocerebrosidase. Pediatrics 96:629–637

Schuening F, Longo W L, Atkinson M E, Zaboikin M (1997) Retrovirus-mediated transfer of the cDNA for human glucocerebrosidase into peripheral blood repopulating cells of patients with Gaucher's disease. Hum Gene Ther 8:2143–2160

Sidransky E, Martin B, Ginns E I (1993) Treatment of Gauchees disease. N Engl J Med 328:1566–1566

Tsai P, Lipton J M, Sahdev I, Najfeld V, Rankin L R, Slyper A H, Ludman M, et al (1992) Allogenic bone marrow transplantation in severe Gaucher disease. Pediatr Res 31:503–507

Tybulewicz V, Tremblay M L, LaMarca M E, Willemsen R, Stubblefield B K, Winfield S, Zablocka B, et al (1992) Animal model of Gaucher's disease from targeted disruption of the mouse glucocerebrosidase gene. Nature 357:407410.

TABLE 1

Sequence of Oligos Used in this Study:

| Oligo Name | Oligo Sequence* (5' to 3') |
| --- | --- |
| SPR2 (SEQ ID NO.: 15) | GCCAGTGTGATGGATATCTGC |
| SPF (SEQ ID NO.: 16) | GACCGATCCAGCCTCCGGACTCT |
| 53GCC2000R (SEQ ID NO.: 17) | GCCGCACACTCTGCTCCCAGAA |
| 3-junction (SEQ ID NO.: 18) | CATCCGTCGCCCACTGCGTGTACTCTCATAGCGGG<u>A</u>A<u>A</u>AA<u>T</u>GT<u>T</u>CCCCAGGGCAGG |
| 5'junction (SEQ ID NO.: 19) | CCTTTGAGTAG<u>A</u>GT<u>CTC</u>CATCATGGCTGGC |

= Bases underlined indicate bases changed in site-directed mutagenesis PCR procedures.

TABLE 2

One of 18 Transient Expression Experiment Comparing the Wild-Type Gcc cDNA (pInex5'3'Gcc) with the Gcc cDNA Modified to Remove the Cryptic Splice Sites (pInexWEIRD)

| Vector | Lac-Z (pmoles/ | Corection Fact (C.F.) | Total Gcc (pmoles/ hr/μg) | Human Gcc (pmoles/ hr/μg) | C.F. X Hum | % pInex 5'3'G |
| --- | --- | --- | --- | --- | --- | --- |
| None | 35 | N/A | 67 | 1.6 | N/A | 15 |
| pInex-5'3'Gcc | 1550 | 1 | 101 | 10.5 | 8.8 | 100 |
| pInex-WEIRD | 185 | 10.1 | 63 | 6.8 | 52.5 | 597 |

SEQUENCE LISTING

```
<160> NUMBER OF SEQ ID NOS: 19

<210> SEQ ID NO 1
<211> LENGTH: 10
<212> TYPE: RNA
<213> ORGANISM: Homo sapiens
<220> FEATURE:
<222> LOCATION: m=1-2
<223> OTHER INFORMATION: m=c or a

<400> SEQUENCE: 1 mmagguaagu                                                          10

<210> SEQ ID NO 2
<211> LENGTH: 41
<212> TYPE: DNA
<213> ORGANISM: Homo sapiens

<400> SEQUENCE: 2
aagccgttga gtagggtaag catcatggct ggcagcctca c                       41

<210> SEQ ID NO 3
<211> LENGTH: 14
<212> TYPE: PRT
<213> ORGANISM: Homo sapiens

<400> SEQUENCE: 3

Lys Pro Leu Ser Arg Val Ser Ile Met Ala Gly Ser Leu Thr
 1               5                  10
```

<210> SEQ ID NO 4
<211> LENGTH: 41
<212> TYPE: DNA
<213> ORGANISM: Homo sapiens

<400> SEQUENCE: 4
aagccgttga gtagagtctc catcatggct ggcagcctca c                          41

<210> SEQ ID NO 5
<211> LENGTH: 15
<212> TYPE: RNA
<213> ORGANISM: Homo sapiens
<220> FEATURE:
<221> NAME/KEY: misc_difference
<222> LOCATION: y=1-10; n=11
<223> OTHER INFORMATION: y=c or u; n=any nucleotide

<400> SEQUENCE: 5
yyyyyyyyyy ncagg                                                      15

<210> SEQ ID NO 6
<211> LENGTH: 40
<212> TYPE: DNA
<213> ORGANISM: Homo sapiens

<400> SEQUENCE: 6
tttcctgccc ttggtacctt cagccgctat gagagtacac                           40

<210> SEQ ID NO 7
<211> LENGTH: 14
<212> TYPE: PRT
<213> ORGANISM: Homo sapiens

<400> SEQUENCE: 7

Phe Pro Ala Leu Gly Thr Phe Ser Arg Tyr Glu Ser Thr Arg
 1               5                  10

<210> SEQ ID NO 8
<211> LENGTH: 40
<212> TYPE: DNA
<213> ORGANISM: Homo sapiens

<400> SEQUENCE: 8
tttcctgccc tgggaacatt ttcccgctat gagagtacac                           40

<210> SEQ ID NO 9
<211> LENGTH: 32
<212> TYPE: DNA
<213> ORGANISM: Homo sapiens

<400> SEQUENCE: 9
aagccgttga gtaggccgct atgagagtac ac                                   32

<210> SEQ ID NO 10
<211> LENGTH: 7
<212> TYPE: PRT
<213> ORGANISM: Homo sapiens

<400> SEQUENCE: 10

Lys Pro Leu Ser Arg Pro Leu
 1               5

<210> SEQ ID NO 11

-continued

```
<211> LENGTH: 1741
<212> TYPE: DNA
<213> ORGANISM: Homo sapiens
<220> FEATURE:
<221> NAME/KEY: CDS
<222> LOCATION: (37)..(1647)
<220> FEATURE:
<221> NAME/KEY: misc_difference
<222> LOCATION: n=1
<223> OTHER INFORMATION: n=any nucleotide

<400> SEQUENCE: 11
ngcggccgct tagcttgact taagaaggcc gacgcc atg gag ttt tca agt cct          54
                                        Met Glu Phe Ser Ser Pro
                                        1               5 tcc aga gag gaa tgt ccc aag cct ttg agt aga gtc tcc atc atg gct         102
Ser Arg Glu Glu Cys Pro Lys Pro Leu Ser Arg Val Ser Ile Met Ala
            10                  15                  20 ggc agc ctc aca ggt ttg ctt cta ctt cag gca gtg tcg tgg gca tca         150
Gly Ser Leu Thr Gly Leu Leu Leu Leu Gln Ala Val Ser Trp Ala Ser
        25                  30                  35 ggt gcc cgc ccc tgc atc cct aaa agc ttc ggc tac agc tcg gtg gtg         198
Gly Ala Arg Pro Cys Ile Pro Lys Ser Phe Gly Tyr Ser Ser Val Val
    40                  45                  50 tgt gtc tgc aat gcc aca tac tgt gac tcc ttt gac ccc ccg acc ttt         246
Cys Val Cys Asn Ala Thr Tyr Cys Asp Ser Phe Asp Pro Pro Thr Phe
55                  60                  65                  70 cct gcc ctg gga aca ttt tcc cgc tat gag agt aca cgc agt ggg cga         294
Pro Ala Leu Gly Thr Phe Ser Arg Tyr Glu Ser Thr Arg Ser Gly Arg
                75                  80                  85 cgg atg gag ctg agt atg ggg ccc atc cag gct aat cac acg ggc aca         342
Arg Met Glu Leu Ser Met Gly Pro Ile Gln Ala Asn His Thr Gly Thr
            90                  95                  100 ggc ctg cta ctg acc ctg cag cca gaa cag aag ttc cag aaa gtg aag         390
Gly Leu Leu Leu Thr Leu Gln Pro Glu Gln Lys Phe Gln Lys Val Lys
        105                 110                 115 gga ttt gga ggg gcc atg aca gat gct gct gct ctc aac atc ctt gcc         438
Gly Phe Gly Gly Ala Met Thr Asp Ala Ala Ala Leu Asn Ile Leu Ala
    120                 125                 130 ctg tca ccc cct gcc caa aat ttg cta ctt aaa tcg tac ttc tct gaa         486
Leu Ser Pro Pro Ala Gln Asn Leu Leu Leu Lys Ser Tyr Phe Ser Glu
135                 140                 145                 150 gaa gga atc gga tat aac atc atc cgg gta ccc atg gcc agc tgt gac         534
Glu Gly Ile Gly Tyr Asn Ile Ile Arg Val Pro Met Ala Ser Cys Asp
                155                 160                 165 ttc tcc atc cgc acc tac acc tat gca gac acc cct gat gat ttc cag         582
Phe Ser Ile Arg Thr Tyr Thr Tyr Ala Asp Thr Pro Asp Asp Phe Gln
            170                 175                 180 ttg cac aac ttc agc ctc cca gag gaa gat acc aag ctc aag ata ccc         630
Leu His Asn Phe Ser Leu Pro Glu Glu Asp Thr Lys Leu Lys Ile Pro
        185                 190                 195 ctg att cac cga gcc ctg cag ttg gcc cag cgt ccc gtt tca ctc ctt         678
Leu Ile His Arg Ala Leu Gln Leu Ala Gln Arg Pro Val Ser Leu Leu
    200                 205                 210 gcc agc ccc tgg aca tca ccc act tgg ctc aag acc aat gga gcg gtg         726
Ala Ser Pro Trp Thr Ser Pro Thr Trp Leu Lys Thr Asn Gly Ala Val
215                 220                 225                 230 aat ggg aag ggg tca ctc aag gga cag ccc gga gac atc tac cac cag         774
Asn Gly Lys Gly Ser Leu Lys Gly Gln Pro Gly Asp Ile Tyr His Gln
                235                 240                 245 acc tgg gcc aga tac ttt gtg aag ttc ctg gat gcc tat gct gag cac         822
Thr Trp Ala Arg Tyr Phe Val Lys Phe Leu Asp Ala Tyr Ala Glu His
```

-continued

```
                   250                 255                 260
aag tta cag ttc tgg gca gtg aca gct gaa aat gag cct tct gct ggg          870
Lys Leu Gln Phe Trp Ala Val Thr Ala Glu Asn Glu Pro Ser Ala Gly
            265                 270                 275 ctg ttg agt gga tac ccc ttc cag tgc ctg ggc ttc acc cct gaa cat          918
Leu Leu Ser Gly Tyr Pro Phe Gln Cys Leu Gly Phe Thr Pro Glu His
        280                 285                 290 cag cga gac tta att gcc cgt gac cta ggt cct acc ctc gcc aac agt          966
Gln Arg Asp Leu Ile Ala Arg Asp Leu Gly Pro Thr Leu Ala Asn Ser
295                 300                 305                 310 act cac cac aat gtc cgc cta ctc atg ctg gat gac caa cgc ttg ctg         1014
Thr His His Asn Val Arg Leu Leu Met Leu Asp Asp Gln Arg Leu Leu
                315                 320                 325 ctg ccc cac tgg gca aag gtg gta ctg aca gac cca gaa gca gct aaa         1062
Leu Pro His Trp Ala Lys Val Val Leu Thr Asp Pro Glu Ala Ala Lys
            330                 335                 340 tat gtt cat ggc att gct gta cat tgg tac ctg gac ttt ctg gct cca         1110
Tyr Val His Gly Ile Ala Val His Trp Tyr Leu Asp Phe Leu Ala Pro
        345                 350                 355 gcc aaa gcc acc cta ggg gag aca cac cgc ctg ttc ccc aac acc atg         1158
Ala Lys Ala Thr Leu Gly Glu Thr His Arg Leu Phe Pro Asn Thr Met
    360                 365                 370 ctc ttt gcc tca gag gcc tgt gtg ggc tcc aag ttc tgg gag cag agt         1206
Leu Phe Ala Ser Glu Ala Cys Val Gly Ser Lys Phe Trp Glu Gln Ser
375                 380                 385                 390 gtg cgg cta ggc tcc tgg gat cga ggg atg cag tac agc cac agc atc         1254
Val Arg Leu Gly Ser Trp Asp Arg Gly Met Gln Tyr Ser His Ser Ile
                395                 400                 405 atc acg aac ctc ctg tac cat gtg gtc ggc tgg acc gac tgg aac ctt         1302
Ile Thr Asn Leu Leu Tyr His Val Val Gly Trp Thr Asp Trp Asn Leu
            410                 415                 420 gcc ctg aac ccc gaa gga gga ccc aat tgg gtg cgt aac ttt gtc gac         1350
Ala Leu Asn Pro Glu Gly Gly Pro Asn Trp Val Arg Asn Phe Val Asp
        425                 430                 435 agt ccc atc att gta gac atc acc aag gac acg ttt tac aaa cag ccc         1398
Ser Pro Ile Ile Val Asp Ile Thr Lys Asp Thr Phe Tyr Lys Gln Pro
    440                 445                 450 atg ttc tac cac ctt ggc cat ttc agc aag ttc att cct gag ggc tcc         1446
Met Phe Tyr His Leu Gly His Phe Ser Lys Phe Ile Pro Glu Gly Ser
455                 460                 465                 470 cag aga gtg ggg ctg gtt gcc agt cag aag aac gac ctg gac gca gtg         1494
Gln Arg Val Gly Leu Val Ala Ser Gln Lys Asn Asp Leu Asp Ala Val
                475                 480                 485 gca ttg atg cat ccc gat ggc tct gct gtt gtg gtc gtg cta aac cgc         1542
Ala Leu Met His Pro Asp Gly Ser Ala Val Val Val Val Leu Asn Arg
            490                 495                 500 tcc tct aag gat gtg cct ctt acc atc aag gat cct gct gtg ggc ttc         1590
Ser Ser Lys Asp Val Pro Leu Thr Ile Lys Asp Pro Ala Val Gly Phe
        505                 510                 515 ctg gag aca atc tca cct ggc tac tcc att cac acc tac ctg tgg cat         1638
Leu Glu Thr Ile Ser Pro Gly Tyr Ser Ile His Thr Tyr Leu Trp His
    520                 525                 530 cgc cag tga tggagcagat actcaaggag gcactgggct cagcctgggc                 1687
Arg Gln
535 attaaaggga cagagtcagc gaattctgca gatatccatc acactggcgg ccgc             1741
```

<210> SEQ ID NO 12
<211> LENGTH: 536

-continued

```
<212> TYPE: PRT
<213> ORGANISM: Homo sapiens

<400> SEQUENCE: 12

Met Glu Phe Ser Ser Pro Ser Arg Glu Glu Cys Pro Lys Pro Leu Ser
  1               5                  10                  15

Arg Val Ser Ile Met Ala Gly Ser Leu Thr Gly Leu Leu Leu Leu Gln
                 20                  25                  30

Ala Val Ser Trp Ala Ser Gly Ala Arg Pro Cys Ile Pro Lys Ser Phe
             35                  40                  45

Gly Tyr Ser Ser Val Val Cys Val Cys Asn Ala Thr Tyr Cys Asp Ser
         50                  55                  60

Phe Asp Pro Pro Thr Phe Pro Ala Leu Gly Thr Phe Ser Arg Tyr Glu
 65                  70                  75                  80

Ser Thr Arg Ser Gly Arg Arg Met Glu Leu Ser Met Gly Pro Ile Gln
                 85                  90                  95

Ala Asn His Thr Gly Thr Gly Leu Leu Leu Thr Leu Gln Pro Glu Gln
                100                 105                 110

Lys Phe Gln Lys Val Lys Gly Phe Gly Gly Ala Met Thr Asp Ala Ala
            115                 120                 125

Ala Leu Asn Ile Leu Ala Leu Ser Pro Pro Ala Gln Asn Leu Leu Leu
        130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Leu Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400
```

```
Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Pro Asn Trp
            420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
                500                 505                 510

Asp Pro Ala Val Gly Phe Leu Glu Thr Ile Ser Pro Gly Tyr Ser Ile
            515                 520                 525

His Thr Tyr Leu Trp His Arg Gln
        530                 535

<210> SEQ ID NO 13
<211> LENGTH: 1741
<212> TYPE: DNA
<213> ORGANISM: Homo sapiens
<220> FEATURE:
<221> NAME/KEY: CDS
<222> LOCATION: (37)..(1647)
<220> FEATURE:
<221> NAME/KEY: misc_difference
<222> LOCATION: n=1
<223> OTHER INFORMATION: n=any nucleotide

<400> SEQUENCE: 13
ngcggccgct tagcttgact taagaaggcc gacgcc atg gag ttt tca agt cct      54
                                       Met Glu Phe Ser Ser Pro
                                        1               5 tcc aga gag gaa tgt ccc aag cct ttg agt aga gtc tcc atc atg gct    102
Ser Arg Glu Glu Cys Pro Lys Pro Leu Ser Arg Val Ser Ile Met Ala
            10                  15                  20 ggc agc ctc aca ggt ttg ctt cta ctt cag gca gtg tcg tgg gca tca    150
Gly Ser Leu Thr Gly Leu Leu Leu Leu Gln Ala Val Ser Trp Ala Ser
        25                  30                  35 ggt gcc cgc ccc tgc atc cct aaa agc ttc ggc tac agc tcg gtg gtg    198
Gly Ala Arg Pro Cys Ile Pro Lys Ser Phe Gly Tyr Ser Ser Val Val
    40                  45                  50 tgt gtc tgc aat gcc aca tac tgt gac tcc ttt gac ccc ccg acc ttt    246
Cys Val Cys Asn Ala Thr Tyr Cys Asp Ser Phe Asp Pro Pro Thr Phe
55                  60                  65                  70 cct gcc ctg gga aca ttt tcc cgc tat gag agt aca cgc agt ggg cga    294
Pro Ala Leu Gly Thr Phe Ser Arg Tyr Glu Ser Thr Arg Ser Gly Arg
                75                  80                  85 cgg atg gag ctg agt atg ggg ccc atc cag gct aat cac acg ggc aca    342
Arg Met Glu Leu Ser Met Gly Pro Ile Gln Ala Asn His Thr Gly Thr
            90                  95                  100 ggc ctg cta ctg acc ctg cag cca gaa cag aag ttc cag aaa gtg aag    390
Gly Leu Leu Leu Thr Leu Gln Pro Glu Gln Lys Phe Gln Lys Val Lys
        105                 110                 115 gga ttt gga ggg gcc atg aca gat gct gct gct ctc aac atc ctt gcc    438
Gly Phe Gly Gly Ala Met Thr Asp Ala Ala Ala Leu Asn Ile Leu Ala
    120                 125                 130
```

```
ctg tca ccc cct gcc caa aat ttg cta ctt aaa tcg tac ttc tct gaa        486
Leu Ser Pro Pro Ala Gln Asn Leu Leu Leu Lys Ser Tyr Phe Ser Glu
135                 140                 145                 150 gaa gga atc gga tat aac atc atc cgg gta ccc atg gcc agc tgt gac        534
Glu Gly Ile Gly Tyr Asn Ile Ile Arg Val Pro Met Ala Ser Cys Asp
                155                 160                 165 ttc tcc atc cgc acc tac acc tat gca gac acc cct gat gat ttc cag        582
Phe Ser Ile Arg Thr Tyr Thr Tyr Ala Asp Thr Pro Asp Asp Phe Gln
            170                 175                 180 ttg cac aac ttc agc ctc cca gag gaa gat acc aag ctc aag ata ccc        630
Leu His Asn Phe Ser Leu Pro Glu Glu Asp Thr Lys Leu Lys Ile Pro
        185                 190                 195 ctg att cac cga gcc ctg cag ttg gcc cag cgt ccc gtt tca ctc ctt        678
Leu Ile His Arg Ala Leu Gln Leu Ala Gln Arg Pro Val Ser Leu Leu
    200                 205                 210 gcc agc ccc tgg aca tca ccc act tgg ctc aag acc aat gga gcg gtg        726
Ala Ser Pro Trp Thr Ser Pro Thr Trp Leu Lys Thr Asn Gly Ala Val
215                 220                 225                 230 aat ggg aag ggg tca ctc aag gga cag ccc gga gac atc tac cac cag        774
Asn Gly Lys Gly Ser Leu Lys Gly Gln Pro Gly Asp Ile Tyr His Gln
                235                 240                 245 acc tgg gcc aga tac ttt gtg aag ttc ctg gat gcc tat gct gag cac        822
Thr Trp Ala Arg Tyr Phe Val Lys Phe Leu Asp Ala Tyr Ala Glu His
            250                 255                 260 aag tta cag ttc tgg gca gtg aca gct gaa aat gag cct tct gct ggg        870
Lys Leu Gln Phe Trp Ala Val Thr Ala Glu Asn Glu Pro Ser Ala Gly
        265                 270                 275 ctg ttg agt gga tac ccc ttc cag tgc ctg ggc ttc acc cct gaa cat        918
Leu Leu Ser Gly Tyr Pro Phe Gln Cys Leu Gly Phe Thr Pro Glu His
    280                 285                 290 cag cga gac tta att gcc cgt gac cta ggt cct acc ctc gcc aac agt        966
Gln Arg Asp Leu Ile Ala Arg Asp Leu Gly Pro Thr Leu Ala Asn Ser
295                 300                 305                 310 act cac cac aat gtc cgc cta ctc atg ctg gat gac caa cgc ttg ctg       1014
Thr His His Asn Val Arg Leu Leu Met Leu Asp Asp Gln Arg Leu Leu
                315                 320                 325 ctg ccc cac tgg gca aag gtg gta ctg aca gac cca gaa gca gct aaa       1062
Leu Pro His Trp Ala Lys Val Val Leu Thr Asp Pro Glu Ala Ala Lys
            330                 335                 340 tat gtt cat ggc att gct gta cat tgg tac ctg gac ttt ctg gct cca       1110
Tyr Val His Gly Ile Ala Val His Trp Tyr Leu Asp Phe Leu Ala Pro
        345                 350                 355 gcc aaa gcc acc cta ggg gag aca cac cgc ctg ttc ccc aac acc atg       1158
Ala Lys Ala Thr Leu Gly Glu Thr His Arg Leu Phe Pro Asn Thr Met
    360                 365                 370 ctc ttt gcc tca gag gcc tgt gtg ggc tcc aag ttc tgg gag cag agt       1206
Leu Phe Ala Ser Glu Ala Cys Val Gly Ser Lys Phe Trp Glu Gln Ser
375                 380                 385                 390 gtg cgg cta ggc tcc tgg gat cga ggg atg cag tac agc cac agc atc       1254
Val Arg Leu Gly Ser Trp Asp Arg Gly Met Gln Tyr Ser His Ser Ile
                395                 400                 405 atc acg aac ctc ctg tac cat gtg gtc ggc tgg acc gac tgg aac ctt       1302
Ile Thr Asn Leu Leu Tyr His Val Val Gly Trp Thr Asp Trp Asn Leu
            410                 415                 420 gcc ctg aac ccc gaa gga gga ccc aat tgg gtg cgt aac ttt gtc gac       1350
Ala Leu Asn Pro Glu Gly Gly Pro Asn Trp Val Arg Asn Phe Val Asp
        425                 430                 435 agt ccc atc att gta gac atc acc aag gac acg ttt tac aaa cag ccc       1398
Ser Pro Ile Ile Val Asp Ile Thr Lys Asp Thr Phe Tyr Lys Gln Pro
    440                 445                 450
```

```
atg ttc tac cac ctt ggc cat ttc agc aag ttc att cct gag ggc tcc      1446
Met Phe Tyr His Leu Gly His Phe Ser Lys Phe Ile Pro Glu Gly Ser
455                 460                 465                 470 cag aga gtg ggg ctg gtt gcc agt cag aag aac gac ctg gac gca gtg      1494
Gln Arg Val Gly Leu Val Ala Ser Gln Lys Asn Asp Leu Asp Ala Val
                475                 480                 485 gca ttg atg cat ccc gat ggc tct gct gtt gtg gtc gtg cta aac cgc      1542
Ala Leu Met His Pro Asp Gly Ser Ala Val Val Val Leu Asn Arg
            490                 495                 500 tcc tct aag gat gtg cct ctt acc atc aag gat cct gct gtg ggc ttc      1590
Ser Ser Lys Asp Val Pro Leu Thr Ile Lys Asp Pro Ala Val Gly Phe
        505                 510                 515 ctg gag aca atc tca cct ggc tac tcc att cac acc tac ctg tgg cat      1638
Leu Glu Thr Ile Ser Pro Gly Tyr Ser Ile His Thr Tyr Leu Trp His
    520                 525                 530 cgc cag tga tggagcagat actcaaggag gcactgggct cagcctgggc              1687
Arg Gln
535 attaaaggga cagagtcagc gaattctgca gatatccatc acactggcgg ccgc          1741
```

<210> SEQ ID NO 14
<211> LENGTH: 536
<212> TYPE: PRT
<213> ORGANISM: Homo sapiens

<400> SEQUENCE: 14

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240
```

-continued

```
Gly Asp Ile Tyr His Gln Thr Trp Ala Arg Tyr Phe Val Lys Phe Leu
            245                 250                 255
Asp Ala Tyr Ala Glu His Lys Leu Gln Phe Trp Ala Val Thr Ala Glu
        260                 265                 270
Asn Glu Pro Ser Ala Gly Leu Leu Ser Gly Tyr Pro Phe Gln Cys Leu
    275                 280                 285
Gly Phe Thr Pro Glu His Gln Arg Asp Leu Ile Ala Arg Asp Leu Gly
290                 295                 300
Pro Thr Leu Ala Asn Ser Thr His His Asn Val Arg Leu Leu Met Leu
305                 310                 315                 320
Asp Asp Gln Arg Leu Leu Leu Pro His Trp Ala Lys Val Val Leu Thr
                325                 330                 335
Asp Pro Glu Ala Ala Lys Tyr Val His Gly Ile Ala Val His Trp Tyr
            340                 345                 350
Leu Asp Phe Leu Ala Pro Ala Lys Ala Thr Leu Gly Glu Thr His Arg
        355                 360                 365
Leu Phe Pro Asn Thr Met Leu Phe Ala Ser Glu Ala Cys Val Gly Ser
    370                 375                 380
Lys Phe Trp Glu Gln Ser Val Arg Leu Gly Ser Trp Asp Arg Gly Met
385                 390                 395                 400
Gln Tyr Ser His Ser Ile Ile Thr Asn Leu Leu Tyr His Val Val Gly
                405                 410                 415
Trp Thr Asp Trp Asn Leu Ala Leu Asn Pro Glu Gly Gly Pro Asn Trp
            420                 425                 430
Val Arg Asn Phe Val Asp Ser Pro Ile Ile Val Asp Ile Thr Lys Asp
        435                 440                 445
Thr Phe Tyr Lys Gln Pro Met Phe Tyr His Leu Gly His Phe Ser Lys
    450                 455                 460
Phe Ile Pro Glu Gly Ser Gln Arg Val Gly Leu Val Ala Ser Gln Lys
465                 470                 475                 480
Asn Asp Leu Asp Ala Val Ala Leu Met His Pro Asp Gly Ser Ala Val
                485                 490                 495
Val Val Val Leu Asn Arg Ser Ser Lys Asp Val Pro Leu Thr Ile Lys
            500                 505                 510
Asp Pro Ala Val Gly Phe Leu Glu Thr Ile Ser Pro Gly Tyr Ser Ile
        515                 520                 525
His Thr Tyr Leu Trp His Arg Gln
    530                 535
```

<210> SEQ ID NO 15
<211> LENGTH: 21
<212> TYPE: DNA
<213> ORGANISM: Artificial Sequence
<220> FEATURE:
<223> OTHER INFORMATION: oligonucleotide

<400> SEQUENCE: 15
gccagtgtga tggatatctg c                                            21

<210> SEQ ID NO 16
<211> LENGTH: 23
<212> TYPE: DNA
<213> ORGANISM: Artificial Sequence
<220> FEATURE:
<223> OTHER INFORMATION: oligonucleotide

<400> SEQUENCE: 16

```
gaccgatcca gcctccggac tct                                              23

<210> SEQ ID NO 17
<211> LENGTH: 22
<212> TYPE: DNA
<213> ORGANISM: Artificial Sequence
<220> FEATURE:
<223> OTHER INFORMATION: oligonucleotide

<400> SEQUENCE: 17
gccgcacact ctgctcccag aa                                               22

<210> SEQ ID NO 18
<211> LENGTH: 51
<212> TYPE: DNA
<213> ORGANISM: Artificial Sequence
<220> FEATURE:
<223> OTHER INFORMATION: oligonucleotide

<400> SEQUENCE: 18
catccgtcgc ccactgcgtg tactctcata gcgggaaaat gtcagggcag g               51

<210> SEQ ID NO 19
<211> LENGTH: 30
<212> TYPE: DNA
<213> ORGANISM: Artificial Sequence
<220> FEATURE:
<223> OTHER INFORMATION: oligonucleotide

<400> SEQUENCE: 19
cctttgagta gagtctccat catggctggc                                       30
```

We claim:

1. An isolated and modified glacocerebrosidase DNA molecule encoding a polypeptide comprising the amino acid sequence of SEQ ID NO:12, wherein said DNA molecule comprises a disruption at a donor splicing site residing in SEQ ID NO: 2 or an acceptor splicing site residinig in SEQ ID NO:6 wherein said disruption prevents splicing of a RNA produced from said DNA molecule, while preserving the ability of said mRNA to encode active glucocerebrosidase.

2. The DNA molecule of claim 1, wherein the DNA molecule is disrupted at both of the donor splicing site residing in SEQ ID NO:2 and the acceptor splicing site residing in SEQ ID NO: 6.

3. The DNA molecule of claim 1, wherein said disruption comprises a mutation as shown in SEQ ID NO:8, or a functionally equivalent mutation.

4. The DNA molecule of claim 1, wherein said disruption comprises a mutation as shown in SEQ ID NO: 4, or a functionally equivalent mutation.

5. The DNA molecule of claim 1, comprising the nucleotide sequence of SEQ ID No:13.

6. A vector comprising the DNA molecule of claim 1 or 5.

7. The vector of claim 6, comprising a promoter that is functional in a mammalian cell.

8. mRNA produced from the DNA molecule of claim 1 or the vector of claim 6.

9. A host cell, or progeny thereof, comprising the nucleic acid molecule of claim 1 or the vector of claim 6.

10. The host cell of claim 9, selected from the group consisting of a mammalian cell, a human cell and a Chinese Hamster Ovary cell.

11. A method for expressing a glucocerebrosidase polypeptide in the host cell of claim 9 comprising culturing the host cell under conditions suitable for DNA molecule expression and recovery of glucocerebrosidase polypeptide.

12. A method for producing a recombinant host cell capable of expressing a glucocerebrosidase nucleic acid molecule, the method comprising introducing into the host cell the vector of claim 6 and recovering the recombinant host cell.

13. A method for producing a transgenic cell that expresses elevated levels of glucocerebrosidase polypeptide relative to a non-transgenic cell, comprising transforming a cell with the vector of claim 9 and recovery of the transgenic cell.

14. A method of producing a genetically transformed cell which expresses or overexpresses a glucocerebrosidase polypeptide, comprising:

(a) preparing a glucocerebrosidase nucleic acid molecule according to claim 1;

(b) inserting the nucleic acid molecule in a vector so that the nucleic acid molecule is operably linked to a promoter;

(c) transfecting a cell with the vector; and (d) recovering the genetically transformed cell.

15. A transgenic cell produced according to the method of claim 14.

16. A method for preventing splicing in a glucocerebrosidase mRNA molecule, comprising modifying at least one nucleotide in a donor splicing site residing in SEQ ID NO:

2 or an acceptor splicing site residing in SEQ ID NO: 6 to disrupt a splicing consensus sequence and prevent splicing of a RNA produced from the DNA molecule, while preserving the ability of said RNA to encode active glucocerebrosidase.

17. The method of claim 16, wherein the modification of the at least one nucleotide comprises mutating the nucleotide to a different nucleotide.

* * * * *